United States Patent
Tam

[19]

[11] Patent Number: 5,926,521
[45] Date of Patent: Jul. 20, 1999

[54] EXACT REGION OF INTEREST CONE BEAM IMAGING USING 3D BACKPROJECTION

[75] Inventor: Kwok Tam, Edison, N.J.

[73] Assignee: Siemens Corporate Research, Inc., Princeton, N.J.

[21] Appl. No.: 09/052,281

[22] Filed: Mar. 31, 1998

[51] Int. Cl.⁶ .................................................. A61B 6/03

[52] U.S. Cl. ................................ 378/4; 378/15; 378/901

[58] Field of Search .................................. 378/4, 15, 901

[56] References Cited

U.S. PATENT DOCUMENTS

| | | | |
|---|---|---|---|
| 5,463,666 | 10/1995 | Eberhard et al. | 378/4 |
| 5,504,792 | 4/1996 | Tam | 378/15 |
| 5,881,123 | 3/1999 | Tam | 378/4 |

OTHER PUBLICATIONS

"Derivation and Implementation of a Cone–Beam Reconstruction Algorithm for Nonplanar Orbits", Kudo et al., IEEE Transactions on Medical Imaging, vol. 13, No. 1, Mar. 1994, pp. 196–211.

*Primary Examiner*—David Vernon Bruce

[57] ABSTRACT

A scanning and data acquisition method and apparatus for three dimensional (3D) computerized tomography (CT) imaging of an object, wherein a plurality of line integral derivatives for a respective plurality of line segments L formed in cone beam projection data acquired on a detector at a plurality of source positions, are calculated. The extent of line segments L in the data acquired at each of the source positions is determined by a mask formed by cone beam projections onto the plane of the detector of portions of the source scan path that are above and below the source position that acquired the cone beam data in which the line integral derivatives for line segments L are being calculated. The line integral derivatives calculated for a plurality of the line segments L are then backprojected onto a 2D space corresponding to the plane of the detector. Finally, the results of the 2D backprojecting step are 3D backprojected into a 3D space, thereby reconstructing a 3D image of the object.

24 Claims, 6 Drawing Sheets

X-RAY SOURCE

EXACT REGION OF INTEREST CONE BEAM IMAGING USING 3D BACKPROJECTION

BACKGROUND OF THE INVENTION

1. Field of the Invention

The invention relates generally to exact image reconstruction in a cone beam imaging system having a radiation source scan path that encircles an object, and more specifically to the use of a 3D backprojection image reconstruction technique in a cone beam imaging system.

2. Description of the Prior Art

A filtered backprojection (FBP) cone beam image reconstruction technique is described by Kudo, H. and Saito, T., in their article entitled "Derivation and Implementation of a Cone-Beam Reconstruction Algorithm for Nonplanar Orbits", IEEE Trans.Med. Imag., MI-13 (1994) 196–211, incorporated herein by reference.

Briefly, the algorithm consists of the following steps at each cone beam view (i.e., at each position of the radiation source as it scans about the object, and at which an imaging detector acquires a corresponding set of measurement data):

1. Compute a 1D projection (i.e., line integral) of the measured cone beam image acquired on a detector plane 1 at each of a plurality of angles θ. This step is illustrated by FIG. 1A for a given angle $\theta_1$ of a plurality of angles θ, where the projection 2 at coordinates (r, θ) comprises the integrated values of the cone beam image 4 on detector plane 1 along plurality of parallel lines L(r, θ) that are normal to angle θ, each line L being at an incremental distance r from an origin O. Generally, if the detector plane 1 comprises an N by N array of pixels, then the number of angles θ is typically given by πN/2.

2. Filter each 1D projection in accordance with a d/dr filter, resulting in a new set of values at each of the r,θ coordinates, such as shown by filtered projection 6 for the angle $\theta_1$ in FIG. 1A.

3. Normalize the filtered projections with a normalization function M(r,θ). Normalization is needed to take into account the number of times the plane of integration Q(r,θ) which intersects the source position and the line L(r,θ), intersects the scan path, since the data developed at each scan path intersection creates a contribution to the image reconstruction on the plane Q(r,θ).

4. Backproject the filtered projection 6 from each angle θ into a 2D object space 7 which coincides with the detector plane 1. This step is illustrated by FIG. 1B, wherein lines 8 spread the value from each r,θ coordinate into 2D space 7 in a direction normal to each θ.

5. Perform a 1D d/dt filtering of the backprojection image formed in 2D space 7 by step 4. The 1D filtering is performed in the direction of the scan path, i.e., along lines 10, where t points in the direction of the scan path.

6. Perform a weighted 3D backprojection of the resulting data in 2D space 7 (i.e., from each pixel in the detector) onto a plurality of sample points P in a 3D object volume 12. The density assigned to each point P is weighted by the inverse of the square of the distance between the point and the x-ray source (see Equation (59) of the forenoted Kudo et al article).

The above prior art procedure will be referred to hereinafter as the 6-step process. It is assumed in this process that the entire cone beam image of the object is captured on the detector of the imaging system. Consider a plane Q(r,θ), which intersects the object, formed by the source and the line L(r,θ) on the detector at angle θ and at a distance r from the origin. Ignoring the function M(r,θ), the operations 1 through 6 compute the contribution to the reconstructed object density on the plane Q(r,θ) from the x-ray data illuminating the plane and its immediate vicinity. Since the algorithm is detector driven, the contribution from the data illuminating the plane is computed every time the plane intersects the scan path and thus is illuminated by the x-ray beam. Thus the function M(r,θ) is used in the filter function in step 2 to normalize the results. This normalization is particularly undesirable since it requires pre-computing and storing a 2D array M(r,θ) for each view (i.e., source position along an imaging scan path), which is both computationally and resource (computer memory) intensive.

Furthermore, since the above procedure assumes that the detector captures the entire cone beam image of the object at each view, it can not be applied to a cone beam imager having a short detector that only captures a portion of the cone beam image at each cone beam view. Thus, in its current form the Kudo et al. FBP technique cannot be applied to a cone beam imager having a spiral scan path and employing a short detector.

SUMMARY OF THE INVENTION

A scanning and data acquisition method and apparatus for three dimensional (3D) computerized tomography (CT) imaging of an object, wherein a plurality of line integral derivatives for a respective plurality of line segments L formed in cone beam projection data acquired on a detector at a plurality of source positions, are calculated. The extent of line segments L in the data acquired at each of the source positions is determined by a mask formed by cone beam projections onto the plane of the detector of portions of the source scan path that are above and below the source position that acquired the cone beam data in which the line integral derivatives for line segments L are being calculated. The line integral derivatives calculated for a plurality of the line segments L are then backprojected onto a 2D space corresponding to the plane of the detector. Finally, the results of the 2D backprojecting step are 3D backprojected into a 3D space, thereby reconstructing a 3D image of the object. As a result, the 3D backprojection approach for cone beam image reconstruction can be applied to a cone beam imager having a scan path geometry that allows the use of a short detector.

DETAILED DESCRIPTION OF THE INVENTION

Figure 2:
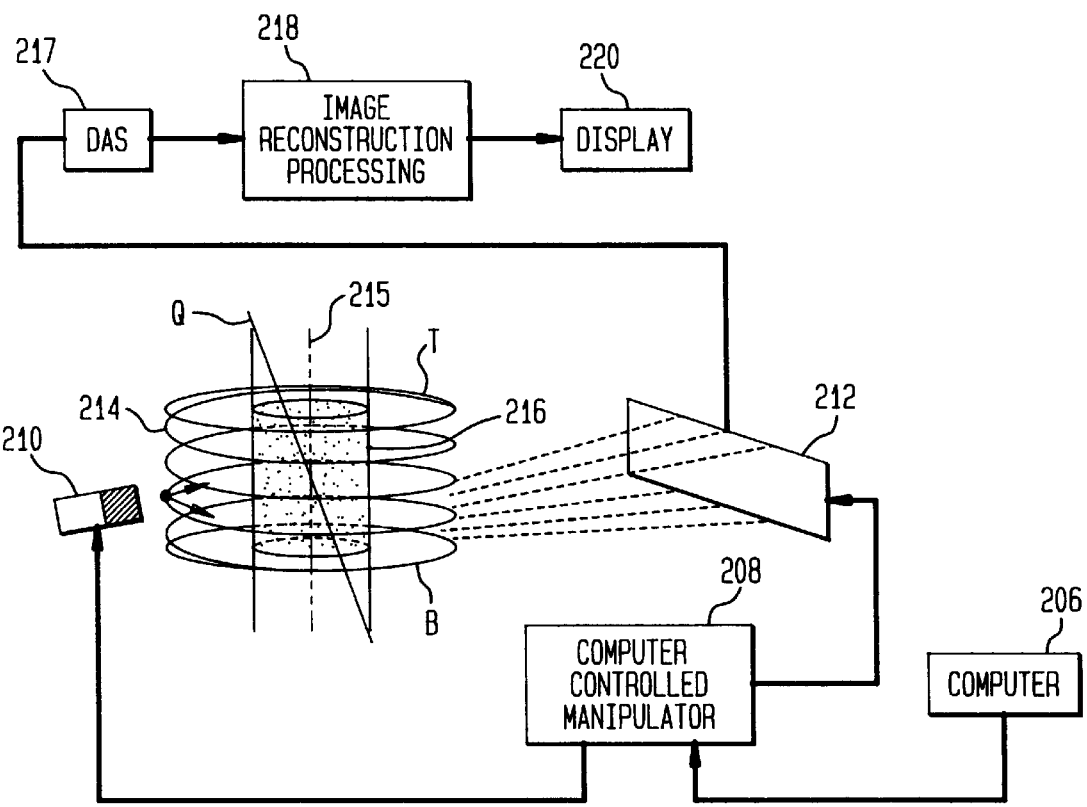
FIG. 2 illustrates a cone beam imaging apparatus useful for performing image reconstruction in accordance with the principles of the invention.

FIG. 2 illustrates a cone beam 3D CT imaging apparatus useful for acquiring and processing acquired measurement data in accordance with the principles of the present invention. The illustrated imaging apparatus is constructed and operates substantially in accordance with same principles described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993 and U.S. Pat. No. 5,453,666 entitled HELICAL AND CIRCLE SCAN REGION OF INTEREST COMPUTERIZED TOMOGRAPHY issued Oct. 31, 1995, incorporated herein by reference, except as to be specifically described later with respect to implementation of image reconstruction processing in accordance with the present invention.

As shown in FIG. 2, a computer controlled manipulator 206, in response to control signals from an appropriately programmed computer 208, cause a source 210 of a cone or pyramid shaped beam of energy (such as x-rays) and a two-dimensional pixelated detector array 212 to cooperate (scan) at a plurality of discreet, sequentially occurring adjacent source positions, along a pre-defined source scanning path. In the illustrated embodiment the scanning path is shown as a spiral scan path 214 centered on a predetermined axis 215 of an object 216. Other types of scan paths that encircle and traverse object 216 can also be used, however, as will become apparent later, a scan path 214 exhibiting a high degree of symmetry in its parallel projection is preferred.

The only height requirement on the detector is that it's height should be more than the distance between adjacent turns of a projection of the spiral scan path on the detector. If only an ROI (Region of Interest) of object 16 is to be imaged, in a preferred embodiment the known technique of providing a top circle scan T at the top level of the ROI and a bottom circle scan B at the bottom level of the ROI are added.

As a result of the source/detector cooperation under control of computer 206 and manipulator 208, at each of the source positions x-ray energy passes through the field of view of the imaging apparatus, is attenuated by object 216, and a set of measurement data corresponding to the sensed x-ray energy falling on the elements (pixels) within detector 212 are developed. The sets of measurement data are then supplied to a data acquisition system (DAS) 217 which, like the previously described portions of FIG. 2, may operate in a fashion well known to those of ordinary skill in this technology for digitizing and storing of the acquired measurement data.

In my above-noted U.S. Pat. No. 5,257,183 and U.S. Pat. No. 5,453,666 image reconstruction processing 218 is provided by Radon space driven conversions, thereby developing an image reconstruction of object 216 on a display 220. It would be desirable to find a way to use the principles of the forenoted Kudo et al. 6-step technique for image reconstruction processor 218 of FIG. 2.

The present inventor has devised a way to incorporate the technique of data combination for ROI reconstruction with the principles of the prior art 6-step algorithm, thereby obviating the need for extensive computations and memory allocation that is required by the normalization step 3 of the 6 step process, and furthermore, allowing such image reconstruction with a detector that does not acquire at each source position a complete view of the ROI of the object.

Accordingly, in accordance with the present invention, instead of division by the function $M(r,\theta)$ as done in the Kudo et al. 6-step process, normalization of the reconstructed object densities is achieved by dividing the x-ray beam coverage of plane $Q(r,\theta)$ between the various source positions that illuminate the plane without any overlap.

Figure 3:
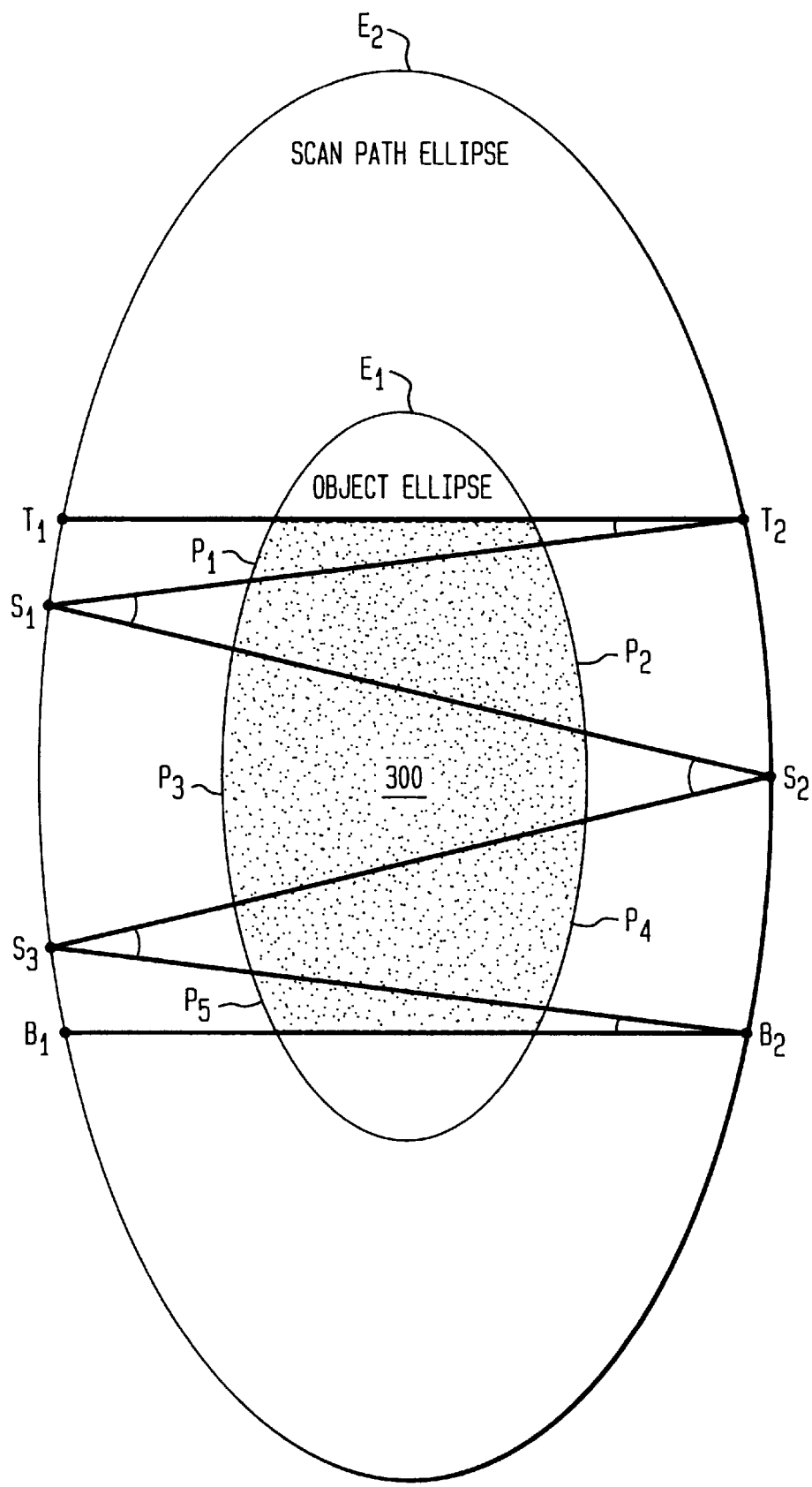
FIG. 3 illustrates a procedure for data combination in accordance with the principles of the invention.

More specifically, this concept of the division of x-ray beam coverage is illustrated in FIG. 3, which represents a typical integration plane $Q(r,\theta)$ intersecting cylindrical object 216 and the spiral scan path 214, which is assumed to wrap around object 216 on an imaginary cylinder. An edge view of plane Q is illustrated in FIG. 2. Since a non-vertical plane will intersect a cylinder in an ellipse, the plane $Q(r,\theta)$ intersects object 216 and the cylindrical spiral scan path 214 in 2 ellipses, one inside the other.

Integration plane Q intersects the object cylinder in the smaller ellipse $E_1$, and it intersects the scan path cylinder in the larger ellipse $E_2$. Since spiral path 214 lies on the scan path cylinder, it intersects the plane Q in points that lie on the ellipse $E_2$. These source positions are shown as $S_1$, $S_2$, and $S_3$ in the FIG. 3. Similarly, it is easy to see that the top scan path circle intersects the plane in two points $T_1$ and $T_2$ which lie at the intersection between $E_2$ and the top edge of the object's region-of-interest (shaded portion of object 216), and that the bottom circle intersects the plane in the two points $B_1$ and $B_2$ which lie at the intersection between $E_2$ and the bottom edge of the object's region-of-interest. Other integration planes may have more or less spiral scan path intersections, depending upon their orientation, and may not intersect either of the top or the bottom circle scan paths.

As is apparent from FIG. 3, the source positions which illuminate that portion of integration plane Q that lies within the region-of-interest (shaded area 300), are $T_2$, $S_1$, $S_2$, $S_3$, and $B_2$. Complete X-ray coverage of region-of-interest 300 of this portion of the integration plane can be achieved by suitably combining the data acquired at these 5 source positions, as indicated in FIG. 3. For example, at $T_2$ we only use the cone beam data within the angle bound by $T_1T_2$ and $S_1T_2$, and at $S_1$ we only use the cone beam data within the angle bound by $T_2S_1$ and $S_2S_1$. And so on. Five partial planes P1 through P5 are therefore defined by the source positions $T_2$, $S_1$, $S_2$, $S_3$, and $B_2$, which do not overlap and together completely cover the portion of plane Q that lies within the region-of-interest of object 216, i.e., ROI 300. In this way the totality of the cone beam data from each of the contributing source positions illuminates the entire plane $Q(r,\theta)$ only once without any overlap. Further details of this data combination technique can be found in my earlier cone beam patents, such as U.S. Pat. No. 5,463,666.

Because only specific non-overlapping contributions to the Radon data are developed from the measurement data, the function $M(r,\theta)$ can be set to unity for all cone beam views. Thus when the detector data from all the views are processed with the 6-step algorithm described above, each plane intersecting the ROI is reconstructed only once.

A summary of the difference between these 2 ways of normalization, that of Kudo et al. as compared with data combination according to the present invention, are summarized and tabulated as follows:

Kudo et al.'s normalization:

$$\int_{\substack{entire \\ plane}} dl = \frac{1}{M}\sum_{i=1}^{M}\int_{\substack{entire \\ plane}} dl$$

Data combination:

$$\int_{\substack{entire \\ plane}} dl = \sum_i \int_{\substack{partial \\ plane\ i}} dl \qquad (5)$$

Next is a description of three modifications that are needed to the 6-step process in order to incorporate the data combination principles of the present invention therein.

Modification 1

Figure 4:
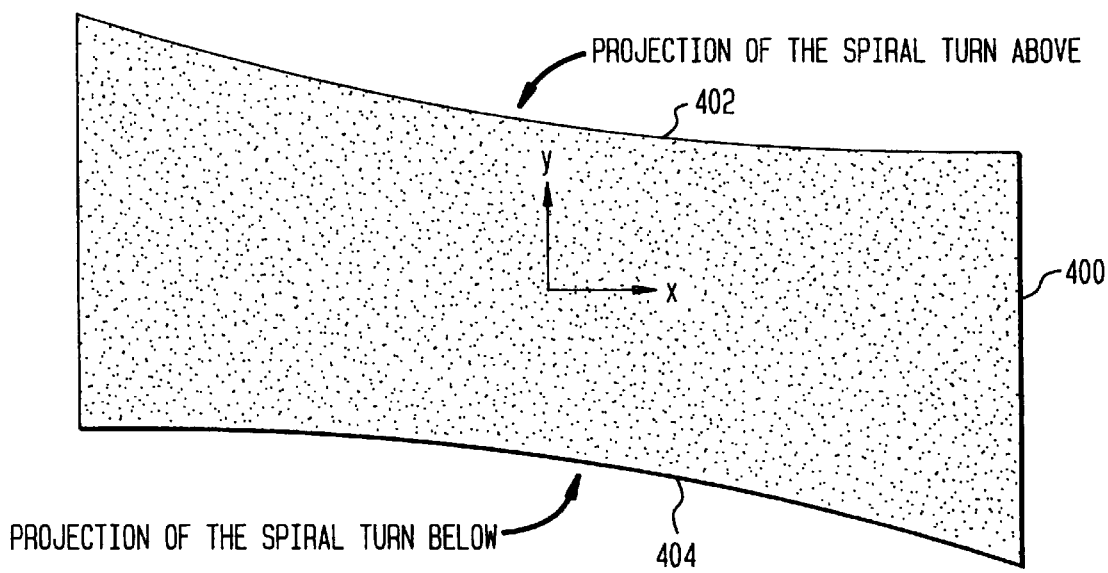
FIGS. 4 and 6–8 illustrate masks useful for processing acquired cone beam measurement data in accordance with the principles of the invention.

The cone beam projection data should be restricted to the appropriate angular range, as described above in conjunction with FIG. 3. This can be accomplished using a masking process. The masking of measurement data is well known, for example see my earlier U.S. Pat. No. 5,504,792 issued Apr. 2, 1996. FIG. 4 illustrates a mask 400 constructed in accordance with the principles of the present invention. Mask 400 consists of a top curve 402 and a bottom curve 404 formed by cone beam projections of the spiral scan path turn above and the spiral scan path turn below the current source position, onto the detector (212 of FIG. 2). For a flat detector located at the rotation axis such that the line connecting the source to the detector origin is normal to the detector plane, the equation for top curve 402 for the spiral scan path projection is given by:

$$y = \frac{h}{2\pi}\tan^{-1}\left(\frac{a}{x}\right)\left(1 + \frac{x^2}{a^2}\right) \qquad \text{for } x \geq 0 \qquad (1)$$

$$y = \frac{h}{2\pi}\left[\pi + \tan^{-1}\left(\frac{a}{x}\right)\right]\left(1 + \frac{x^2}{a^2}\right) \qquad \text{for } x < 0$$

where x and y are the Cartesian coordinate axes of the detector with the y axis coinciding with the rotation axis, a is the radius of the spiral, and h is the distance between adjacent spiral turns (the pitch). Bottom curve 404 is a reflection of top curve 402 about the origin, i.e. (x,y)→(−x, −y).

Figure 5:
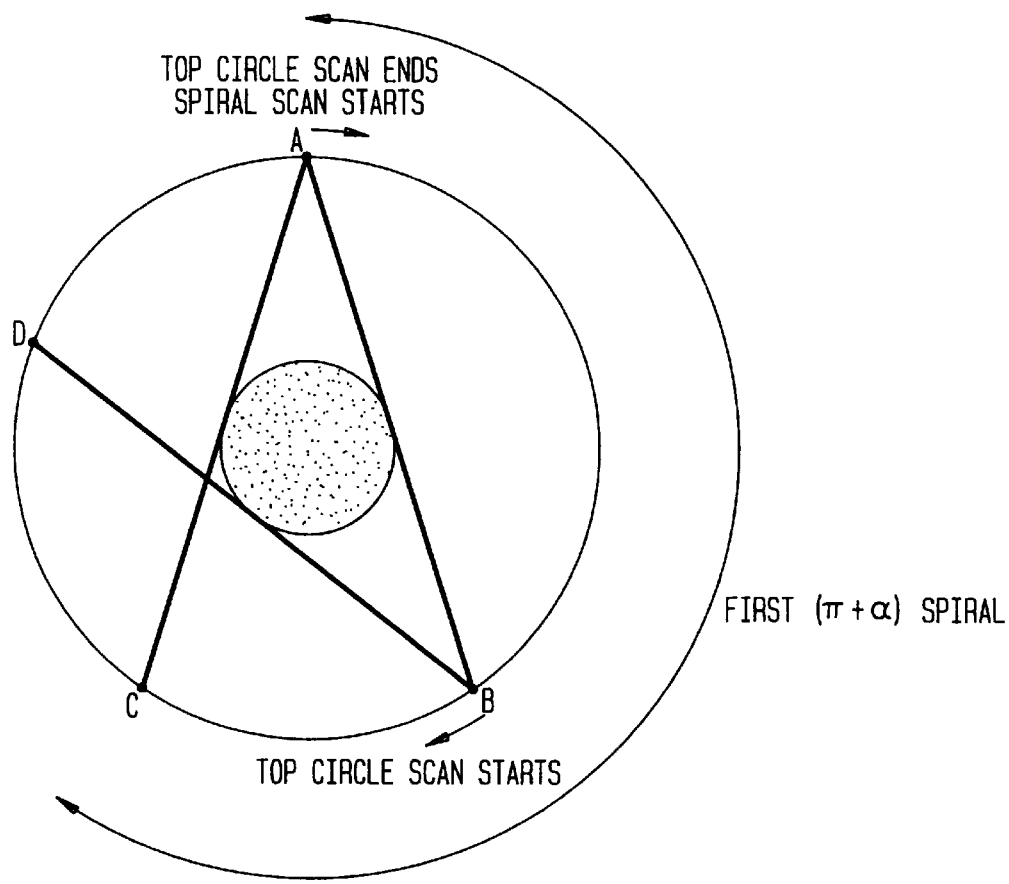
FIG. 5 is useful for understanding the generation of the masks shown in FIGS. 6–8.
Figure 6:
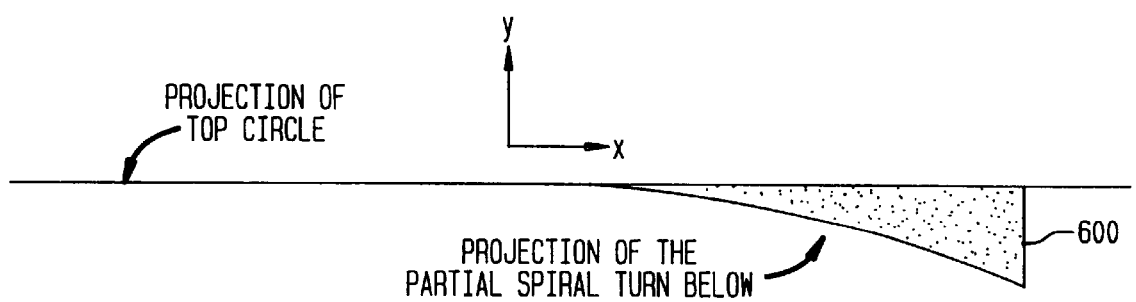
Figure 7:
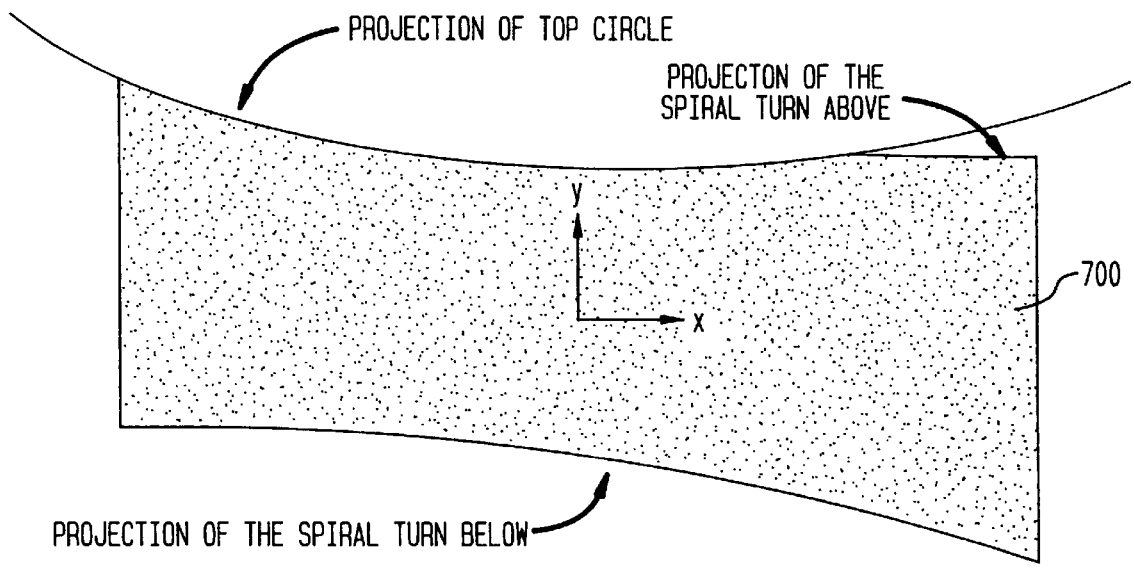

As described in conjunction with FIG. 2, for ROI imaging, circular arc scans are needed at the top and bottom levels. The top circle scan T starts at the angle (π+α) before the start of the spiral scan, and the bottom circle scan B ends at the angle (π+α) after the end of the spiral scan, where a is the fan angle of the x-ray beam. The detailed geometry of the precise mask used at each source position depends on the location of the source in the scan path. Accordingly, one can divide the spiral scan path into 5 distinct regions, as illustrated in FIG. 5. The first region, (1), comprises the last (π+α) turn of the top circle. The second region, (2), comprises the first (π+α) turn of the spiral. The third region, (3), comprises the interior portion of the spiral, i.e. after the first (π+α) turn and before the last (π+α) turn. The fourth region, (4), comprises the last (π+α) turn of the spiral. The fifth region, (5), comprises the first (π+α) turn of the bottom circle. The masks for these 5 regions are described in greater detail below, and are illustrated in FIGS. 6–7. These Figures assume the source rotates in a spiral path from top to bottom in a clockwise direction.

(1) For the last (π+α) turn of the top circle, see mask 600 of FIG. 6, wherein:

Top curve: a horizontal line at the level of the top circular arc; and

Bottom curve: a reflection of Equation (1) about the origin.

(2) For the first (π+α) turn of the spiral, see mask 700 of FIG. 7, wherein:

Top curve: the intersection of two curves: the standard top spiral mask, Equation (1), and the cone beam projection of the top circle projected from the source given by the equation:

$$y = b\left(1 + \frac{x^2}{a^2}\right)$$

where 2b is the distance between the top and bottom circles.

Bottom curve: reflection of Equation (1) about the origin (3) For the interior portion of the spiral, see mask 400 of FIG. 4, wherein:

Top curve: Equation (1)

Bottom curve: reflection of Equation (1) about the origin (4) For the last (π+α) turn of the spiral, see mask 700 of FIG. 7, but rotated by 180°.

(5) For the first (π+α) turn of the bottom circle, see mask 600 of FIG. 6, but rotated by 180°.

Figure 1A:
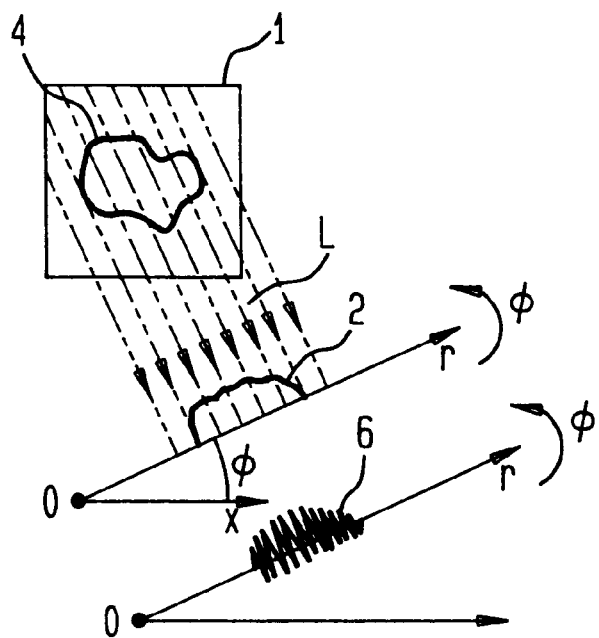
FIGS. 1A and 1B describe a prior art 3D backprojection approach for cone beam image reconstruction.
Figure 1B:
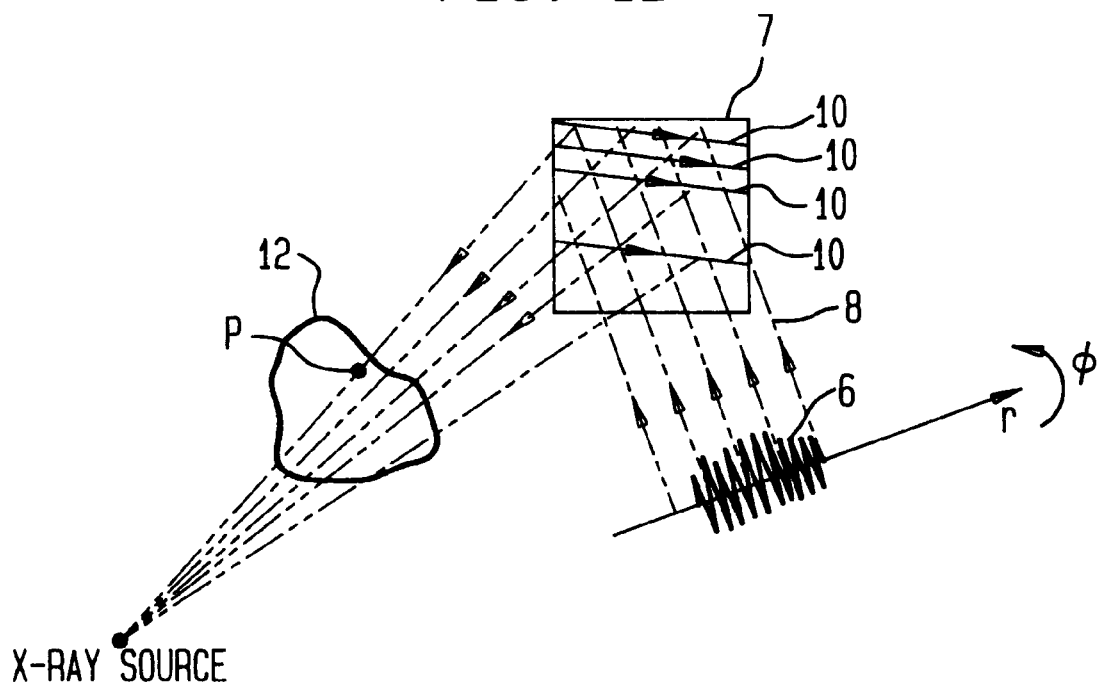

In accordance with the principles of the invention, to incorporate the principles of the 6-step process into a cone beam imaging apparatus having a short detector, the projections of lines L illustrated in FIG. 1A, instead of being computed across the full length of detector 1, are required to be bound by the masks of FIGS. 4 and 6–7. Since the masks are formed by cone beam projection of the spiral turn above and the turn below the current source position, the masked segment corresponds exactly to the angular range bound by the prior and the subsequent source positions, as required by the data combination principles illustrated in FIG. 3. Computer 206 of FIG. 2 can compute masks 400 on the fly during image reconstruction, or they could be pre-calculated and stored in system memory.

Modification 2

Figure 8:
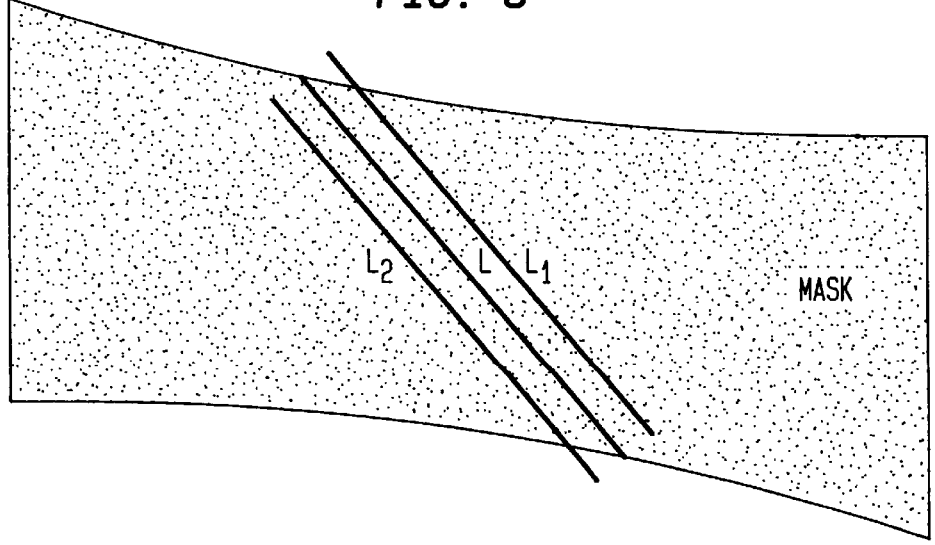

Steps 1 and 2 of the prior art 6 step process are intended to yield a quantity proportional to the Radon derivative for the integration plane $Q(r,\theta)$, as generally used in the Radon space driven version of image reconstruction processing. Using the data combination technique, the Radon derivative for the relevant portion of integration plane $Q(r,\theta)$ should be computed as illustrated in FIG. 8. L, $L_1$ and $L_2$ are three closely spaced parallel line segments, with L being bound by the mask, as described above in modification 1, and positioned midway between $L_1$ and $L_2$. The line segments $L_1$ and $L_2$ are obtained by translating L orthogonally by a small spacing. The difference between the integrals computed on $L_1$ and $L_2$ yields the correct Radon derivative, up to a multiplicative constant. The general theory behind this operation is described in the forenoted U.S. Pat. No. 5,257,183. A preferred improved technique is described in U.S. Ser. No. 08/771,401, entitled METHOD AND APPARATUS FOR ELIMINATING BOUNDARY ERRORS IN CONE BEAM IMAGING, filed Dec. 20, 1996, incorporated herein by reference, wherein detector rows adjacent the top and bottom of the detector are used to calculate line integrals for the line segments $L_1$, $L_2$.

Modification 3

Figure 9:
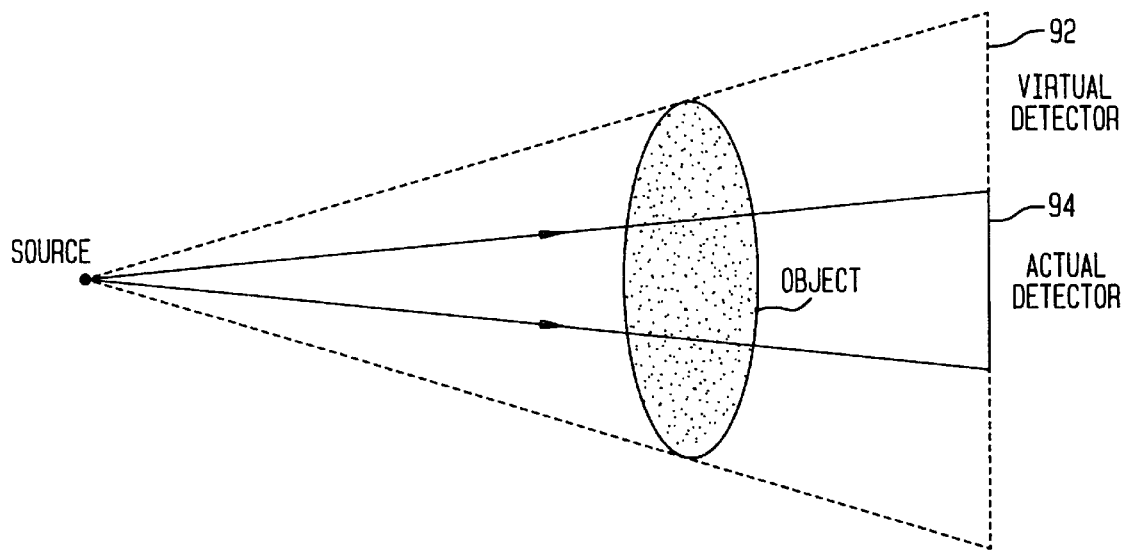
FIG. 9 illustrates a backprojection procedure in accordance with the principles of the invention.

Step 4 of the prior art 6 step process is modified by backprojecting the filtered projection 6 from each angle θ onto a virtual detector which is enlarged (compared with detector 1 of FIG. 1A), to cover the entire field of view of an ROI in the object, instead of just backprojecting onto the actual detector (which is usually shorter than the virtual detector). This is illustrated in FIG. 9 wherein at a source position centered with respect to the ROI in the object, 92 illustrates the height of the virtual detector used to cover the entire field-of-view of the ROI in the object and 94 illustrates the height of the actual detector used to acquire the measurement data (i.e., detector 212 of FIG. 2). This modification is needed because the Radon data corresponding to each partial plane P1 through P5 affects the reconstruction of the entire plane Q not just the partial plane itself Consequently the following 2 steps in the 6-step algorithm, viz. 5 and 6, should also be performed with the back projected image on the virtual detector.

Thus, there has been shown and described a novel method and apparatus for allowing the use of 3D backprojection image reconstruction techniques in a cone beam CT imaging apparatus having a relatively small detector. Many changes, modifications, variations and other uses and applications of the subject invention will, however, become apparent to those skilled in the art after considering this specification and its accompanying drawings, which disclose preferred embodiments thereof All such changes, modifications, variations and other uses and applications which do not depart from the teachings herein are deemed to be covered by this patent, which is limited only by the claims which follow as interpreted in light of the foregoing description.

I claim:

1. A method for performing three dimensional computerized tomography imaging of a region-of-interest (ROI) in an object using a cone beam source of radiation energy, comprising the steps of:

defining a source scanning trajectory as a scan path traversed by the source;

using the cone beam source, fixed relative to an area detector with both source and detector movably positioned relative to the object, to apply radiation energy towards the object from a plurality of source positions along the scan path as said source traverses the scan path, and cause said area detector to acquire cone beam projection data corresponding to respective portions of the object at each of said source positions;

calculating a line integral derivative for each of a plurality of line segments L formed in the cone beam projection data acquired at each of said source positions, the extent of said line segments L in the cone beam data acquired at a given one of said source positions being determined by a mask formed by cone beam projections onto the plane of the detector of portions of the source scan path that are above and below the given one of said source positions;

2D backprojecting the line integral derivatives calculated for a plurality of said line segments L onto a 2D space corresponding to the plane of the detector; and 3D backprojecting the results of the 2D backprojecting step into a 3D space, thereby reconstructing a 3D image of the ROI in the object.

2. The method of claim 1, wherein the calculating step calculates line integral derivatives for a plurality of line segments L spaced along each of a plurality of lines (r, θ), each line having a different angular position, θ, with respect to the coordinate system of the detector.

3. The method of claim 1, wherein the calculating step uses a mask formed for each source position that has a top curve and a bottom curve, with the extent of said line segments L for which the line integral derivatives are calculated in the cone beam projection data being bound between the top curve and the bottom curve of the mask.

4. The method of claim 3, wherein the source scanning trajectory is defined as a spiral scan path that surrounds the ROI in the object, and is connected to a first scan path circle at a top portion of the ROI in the object, and a second scan path circle at a bottom portion of the ROI in the object.

5. The method according to claim 4, wherein at source positions of the scan path at the top of the ROI in the object, the top curve of the mask includes a horizontal line portion formed from a projection of the first scan path circle, and the bottom curve of the mask is formed from a projection of the spiral scan path.

6. The method according to claim 4, wherein at source positions of the scan path at the bottom of the ROI in the object, the top curve of the mask is formed from a projection of the spiral scan path, and the bottom curve of the mask includes a horizontal line portion formed from a projection of the second scan path circle.

7. The method according to claim 5, wherein the top curve is formed from an intersection of a projection of the first scan path circle and a projection of the spiral scan path.

8. The method according to claim 6, wherein the bottom curve is formed from an intersection of a projection of the second scan path circle and a projection of the spiral scan path.

9. The method of claim 1, wherein after completion of the 2D backprojecting step, a 1D d/dt filtering step is performed on the results in said 2D space along lines in the direction of the scan path.

10. The method of claim 9, wherein the 3D backprojecting step comprises performing a weighted 3D backprojection of the 1D d/dt filtering results at discrete points along said lines onto a plurality of sample points in a 3D object volume.

11. The method of claim 10, wherein the weight assigned to each sample point in the 3D object volume is the inverse of the square of the distance between each sample point and a virtual location for the radiation source in the 3D volume.

12. The method of claim 1, wherein the 2D backprojecting step comprises 2D backprojecting the calculated line integral derivatives onto a virtual 2D space having a height that is greater than the height of said area detector.

13. The method of claim 12, wherein the height of said virtual 2D space is sufficient to cover the entire field-of-view of the ROI in the object.

14. Apparatus for performing three dimensional computerized tomography imaging of a region-of-interest (ROI) in an object using a cone beam source of radiation energy, comprising:

a source of cone beam radiation energy;

a manipulator for providing a source scanning trajectory as a scan path that encircles the ROI in the object and causes the source and detector to traverse the scan path;

means for causing the source to apply radiation energy towards the object from a plurality of source positions along the scan path as said source traverses the scan path, said area detector acquiring cone beam projection data corresponding to respective portions of the object at each of said source positions; and an image reconstruction processor for, calculating a line integral derivative for each of a plurality of line segments L formed in the cone beam projection data acquired at each of said source positions, the extent of said line segments L in the cone beam data acquired at a given one of said source positions being determined by a mask calculated by said image reconstruction processor that corresponds to the shape of cone beam projections onto the plane of the detector of portions of the source scan path that are above and below the given one of said source positions, 2D backprojecting the line integral derivatives calculated for a plurality of said line segments L onto a 2D space corresponding to the plane of the detector, and 3D backprojecting the 2D backprojection results into a 3D space, thereby reconstructing a 3D image of the ROI in the object.

15. The apparatus of claim 14, wherein the mask calculated for each source position that has a top curve and a bottom curve, with the extent of said line segments L for which the line integral derivatives are calculated in the cone beam projection data being bound between the top curve and the bottom curve of the mask.

16. The apparatus of claim 15, wherein the manipulator defines the source scanning trajectory as a spiral scan path the surrounds the ROI in the object, and is connected to a first scan path circle at a top portion of the ROI in the object, and a second scan path circle at a bottom portion of the ROI in the object.

17. The apparatus of claim 16, wherein the mask calculated at source positions of the scan path at the top of the ROI in the object has a top curve that includes a horizontal line portion formed from a projection of the first scan path circle, and the bottom curve of the mask is formed from a projection of the spiral scan path.

18. The apparatus of claim 16, wherein the mask calculated at source positions of the scan path at the bottom of the ROI in the object has a top curve that is formed from a projection of the spiral scan path, and a bottom curve that includes a horizontal line portion formed from a projection of the second scan path circle.

19. The apparatus of claim 17, wherein the top curve is formed from an intersection of a projection of the first scan path circle and a projection of the spiral scan path.

20. The apparatus of claim 18, wherein the bottom curve is formed from an intersection of a projection of the second scan path circle and a projection of the spiral scan path.

21. The apparatus of claim 14, wherein said image reconstruction processor performs a 1D d/dt filtering on the 2D backprojection results in said 2D space along lines extending in the direction of the scan path, before beginning the 3D backprojecting.

22. The apparatus of claim 21, wherein said image reconstruction processor performs the 3D backprojecting by performing a weighted 3D backprojection of the 1D d/dt filtering results at discrete points along said lines onto a plurality of sample points in a 3D object volume.

23. The apparatus of claim 14, wherein said image reconstruction processor performs the 2D backprojecting by 2D backprojecting the calculated line integral derivatives onto a virtual 2D space having a height that is greater than the height of said area detector.

24. The apparatus of claim 23, wherein the height of said virtual 2D space covers the entire field-of-view of the ROI in the object.

* * * * *